United States Patent [19]

Bender et al.

[11] Patent Number: 4,847,270

[45] Date of Patent: Jul. 11, 1989

[54] INHIBITION OF THE 5-LIPOXYGENASE PATHWAY UTILIZING CERTAIN 2,2'-ALKYLDIYL BIS(THIO)BIS-IMIDAZOLES AND DERIVATIVES

[75] Inventors: Paul E. Bender, Cherry Hill, N.J.; David T. Hill, North Wales, Pa.

[73] Assignee: SmithKline Beckman Corporation, Philadelphia, Pa.

[21] Appl. No.: 119,117

[22] Filed: Nov. 10, 1987

Related U.S. Application Data

[60] Division of Ser. No. 856,735, Apr. 28, 1986, Pat. No. 4,728,656, which is a continuation-in-part of Ser. No. 808,396, Dec. 12, 1985, abandoned.

[51] Int. Cl.$^4$ .................. A61K 31/415; C07D 401/14
[52] U.S. Cl. ..................................... 514/333; 514/341; 546/256; 548/337
[58] Field of Search ................ 514/333, 341; 546/256; 548/337

[56] References Cited

U.S. PATENT DOCUMENTS

| | | | |
|---|---|---|---|
| 4,188,397 | 2/1980 | Hill | 548/336 |
| 4,339,583 | 7/1982 | Cross et al. | 546/256 |
| 4,728,656 | 3/1988 | Bender et al. | 514/333 |

FOREIGN PATENT DOCUMENTS

| | | | |
|---|---|---|---|
| 005545 | 11/1979 | European Pat. Off. | 548/337 |
| 1178242 | 1/1970 | United Kingdom | 548/337 |

*Primary Examiner*—Alan L. Rotman
*Attorney, Agent, or Firm*—Nancy S. Mayer; Carol G. Canter; Janice E. Williams

[57] ABSTRACT

Novel compounds, pharmaceutical compositions and a method of inhibiting the 5-lipoxygenase products in an animal in need thereof which comprises administering an effective, 5-lipoxygenase pathway inhibiting amount of a 2,2'-[1,2-ethanediylbis-(thio)]-bis-1H-imidazole or 2,2'-[1,3-propan-2-onediylbis-(thio)]bis-1H-imidazole, or a pharmaceutically acceptable salt thereof, to such animal.

8 Claims, No Drawings

INHIBITION OF THE 5-LIPOXYGENASE PATHWAY UTILIZING CERTAIN 2,2'-ALKYLDIYL BIS(THIO)BIS-IMIDAZOLES AND DERIVATIVES

CROSS REFERENCE TO RELATED APPLICATIONS

This is a divisional of application Ser. No. 856,735 filed Apr. 28, 1986 now U.S. Pat. No. 4,728,656 which is a continuation-in-part of Ser. No. 808,396 filed Dec. 12, 1985, now abandoned.

BACKGROUND OF THE INVENTION

This invention relates to novel compounds, pharmaceutical compositions and a method of inhibiting the 5-lipoxygenase pathway of arachidonic acid metabolism in an animal in need thereof which comprises administering to such animal an effective, 5-lipoxygenase pathway inhibiting amount of a 2,2-[1,2-ethanediyl-bis-(thio)bis-1H-imidazole, a 2,2-[1,3-propan-2-onediylbis(thio)]bis-1H-imidazole or a pharmaceutically acceptable salt thereof.

Hill, U.S. Pat. No. 4,188,397, issued Feb. 12, 1980 discloses compounds of the formula

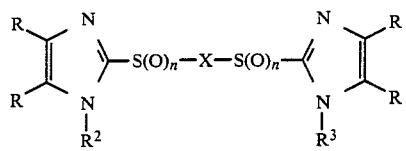

wherein:

R is 4-monosubstituted phenyl wherein said substituent is selected from methoxy, methylthio, trifluoromethyl, chloro, fluoro, bromo or methylenedioxy when taken with an adjacent position on the phenyl ring;

$R^2$ and $R^3$ are both H or one is H and the other is $CH_3$;

n is 0, 1 or 2; and

X is, among others, $(CH_2)_2$ and $CH_2C(O)CH_2$. Hill also discloses that such compounds are useful as antiarthritic agents, as confirmed by their ability to inhibit adjuvant induced polyarthritis in rats; and are also useful to regulate cell mediated immunity, as confirmed by the oxazolone-induced contact sensitivity test procedure which measures changes in mouse paw edema produced by administration of test compounds.

The adjuvant-induced polyarthritis assay in rats is useful in detecting compounds which are inhibitors of prostanoid synthesis, mediated by the prostanoids formed by the enzyme cyclooxygenase, but is of no known utility in detecting or suggesting compounds which are inhibitors of the generation of 5-lipoxygenase products (such as HETES, $LTB_4$ and peptidoleukotrienes). The oxazolone-induced contact sensitivity test in which mouse paw volume is measured is useful in detecting compounds which are immunostimulatory, but is of no known utility in detecting or suggesting compounds which are inhibitors of the 5-lipoxygenase pathway.

SUMMARY OF THE INVENTION

This invention relates to a compound of the formula:

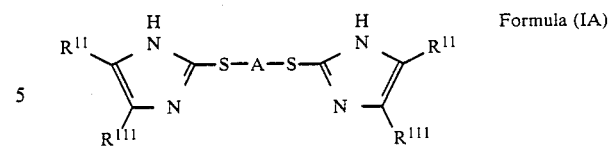

wherein:

A is $CH_2CH_2$ or $CH_2C(O)CH_2$; and $R^{11}$ and $R_{111}$ are both pyridyl or one of $R^{11}$ and $R^{111}$ is pyridyl and the other is monosubstituted phenyl wherein said substituent is selected from halo; or a pharmaceutically acceptable salt thereof.

This invention relates to a pharmaceutical composition comprising an effective, non-toxic 5-lipoxygenase pathway inhibiting amount of a compound of Formula (IA), or a pharmaceutically acceptable salt thereof, and a pharmaceutically acceptable carrier or diluent.

This invention also relates to a method of treating a 5-lipoxygenase pathway mediated disease in an animal in need thereof, provided that such animal is in need of treatment of a 5-lipoxygenase pathway mediated disease other than rheumatoid arthritis, which comprises administering to such animal an effective, non-toxic 5-lipoxygenase pathway inhibiting amount of a compound of the formula

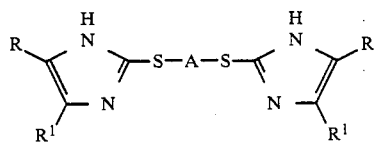

wherein:

A is $CH_2CH_2$ or $CH_2C(O)CH_2$; and

R and $R^I$ are independently selected from pyridyl or monosubstituted phenyl wherein said substituent is selected from halo; or a pharmaceutically acceptable salt thereof.

DETAILED DESCRIPTION OF THE INVENTION

It will be apparent to one of skill in the art that all the compounds of Formula (IA) are encompassed by the scope of Formula (I). All the compounds of Formula (I) are useful in treating a 5-lipoxygenase pathway mediated disease in an animal in need thereof by inhibiting the 5-lipoxygenase pathway.

The preparation of compounds of Formula (I), other than those of Formula (IA) is disclosed in Hill, U.S. Pat. No. 4,188,397, issued Feb. 12, 1980, the disclosure of which is hereby incorporated by reference. Preparation of compounds of Formula (IA) is accomplished by reacting the appropriate 4/5-(pyridyl)-5/4(pyridyl/halo substituted phenyl)-[1H]-imidazole-2-thione [which can be prepared by the method of Lantos et al., *J. Med. Chem*, 27, 72–75 (1984), or alternately by the method of Ciba Geigy, U.K. Patent Application GB No. 2,039,882, with either 1-3-dihalopropanone or 1,2-dihaloethane in methanol.

Preferred compounds of Formula (I) include 2,2'-[ethanediylbis(thio)]bis[4,5-bis(4-fluorophenyl)-1H-imidazole]; 2,2'-[1,3-propan-2-onediylbis(thio)]bis[4-(4-fluoro-phenyl)-5-(4-pyridyl)-1H-imidazole]; and 2,2'-[1,3-propan-2-onediylbis(thio)]bis[4,5-bis-(4-fluorophenyl)-1H-imidazole].

Pharmaceutically acceptable salts and their preparation are well known to those skilled in pharmaceuticals. Pharmaceutically acceptable salts of the compounds of Formula (I) which are useful in the present invention include, but are not limited to, hydrochloride, hydrobromide maleate, fumarate, lactate, oxalate, methanesulfonate, ethanesulfonate, benzenesulfonate, tartrate, citrate, sulfate, phosphate and nitrate salts. Preparation of such salts for some Formula (I) compounds is disclosed in Hill, U.S. Pat. No. 4,188,397.

It is known that some of the compounds of Formula (I) are useful for treating cyclooxygenase product-mediated disease states. It has now been discovered that all of the compounds of Formula (I) are also useful for treating disease states mediated by the 5-lipoxygenase pathway by inhibiting the 5-lipoxygenase pathway. The discovery that the compounds of Formula (I) are inhibitors of the 5-lipoxygenase pathway is based on the effects of the compounds of Formula (I) and on the production of 5-lipoxygenase products by inflammatory cells in vitro in assays, some of which are described in the Examples. These data, together with previous observations on the anti-edematous effects of some of the compounds of Formula (I) in inflammatory lesions caused by cyclooxygenase-generated products, reveal that compounds of Formula (I) inhibit the 5-lipoxygenase pathway of arachidonic acid metabolism by showing that they impair the production of 5-lipoxygenase products such as leukotriene $B_4$ (di-HETE) and 5-HETE production by RBL-1 cells.

The pathophysiological role of arachidonic acid metabolites has been the focus of recent intensive studies. In addition to the well-described phlogistic activity (i.e. general inflammatory activity) of prostaglandins, the more recent description of similar activity for eicosanoids has broadened the interest in these products as mediators of inflammation [See, O'Flaherty, *Lab. Invest.*, 47, 314–329 (1982)]. The reported discovery of potent chemotactic and algesic activity for $LTB_4$ [see, Smith, *Gen. Pharmacol.*, 12, 211–216 (1981) and Levine et al., *Science*, 225, 743–745 (1984)], together with known $LTC_4$ and $LTD_4$-mediated increase in capillary permeability [see, Simmons et al., *Biochem. Pharmacol.*, 32, 1353–1359 (1983), Veno et al., *Prostaglandins*, 21, 637–647 (1981), and Camp et al., *Br. J. Pharmacol.*, 80, 497–502 (1983)], has led to their consideration as targets for phrmacological intervention in both the fluid and cellular phases of inflammatory diseases.

The pharmacology of several inflammatory model systems has attested to the effectiveness of corticosteroids in reducing the cellular infiltration. These results, and the observation that corticosteroids inhibit the generation of both cyclooxygenase and lipoxygenase products, suggest that such dual inhibitors may effectively reduce both the fluid and cellular phases of the inflammatory response since selective cyclooxygenase inhibitors do not reliably inhibit cell influx into inflammatory sites [See, Vinegar et al., *Fed. Proc.*, 35, 2447–2456 (1976), Higgs et al., *Brit. Bull.*, 39, 265–270 (1983), and Higgs et al., *Prostaglandins, Leukotrienes and Medicine*, 13, 89–92 (1984)]. The observations outlined above cogently argue that a dual inhibitor of arachidonic acid metabolism would be a more effective antiinflammatory agent than an inhibitor of cyclooxygenase only. Under optimal conditions, it is likely that an agent with preferential lipoxygenase inhibitory activity would not share the ulcerogenic liability of cyclooxygenase inhibitors or the toxicity of corticosteroids.

Recent clinical data also support the enthusiasm for 5-lipoxygenase pathway inhibitors of arachidonic acid metabolism in a variety of inflammatory diseases in which granulocyte and/or monocyte infiltration is prominent. The reported demonstration of elevated levels of $LTB_4$ in rheumatoid arthritic joint fluid [See, Davidson et al., *Ann. Rheum. Dis.*, 42, 677–679 (1983)] also suggests a contributing role for arachidonic acid metabolites in rheumatoid arthritis. The recently reported preliminary observation of efficacy, including remission, reported with sulfasalazine treatment of rheumatoid arthritic patients [See Neumann et al., *Brit. Med. J.*, 287, 1099–1102 (1983)] illustrates the utility of inhibitors of the 5-lipoxygenase pathway in rheumatoid arthritis.

Sulfasalazine, which is used for treatment of ulcerative colitis, has been reported to inhibit $LTB_4$ and 5-HETE production in vitro [See, Stenson et al., *J. Clin. Invest.*, 69, 494–497 (1982)]. This observation, coupled with the fact that it has been reported that inflamed gastrointestinal mucosa from inflammatory bowel disease patients showed increased production of $LTB_4$ [See, Sharon et al., *Gastroenterol.*, 84, 1306 (1983)], suggests that sulfasalazine can be effective by virtue of inhibition of production of chemotactic eicosanoids (such as the 5-lipoxygenase pathway product known as $LTB_4$). The observations serve to underscore utility of inhibitors of the 5-lipoxygenase pathway in inflammatory bowel disease.

Another area of utility for inhibitors of the 5-lipoxygenase pathway is in the treatment of psoriasis. It was demonstrated that involved psoriatic skin had elevated levels of $LTB_4$ [See, Brain et al., *Lancet*, 19, Feb. 19, 1983]. The promising effect of benoxaprofen on psoriasis [See, Allen et al., *Brit. J. Dermatol.*, 109, 126–129 (1983)], a compound with in vitro lipoxygenase inhibitory activity on psoriasis, lends support to the concept that 5-lipoxygenase pathway inhibitors can be useful in the treatment of psoriasis.

Lipoxygenase products have been identified in exudate fluids from gouty patients. This disorder is characterized by massive neutrophil infiltration during the acute inflammatory phases of the disease. Since a major 5-lipoxygenase product, $LTB_4$, is produced by neutrophils, it follows that inhibition of the synthesis of $LTB_4$ can block an amplification mechanism in gout.

Another area in which inhibitors of the 5-lipoxygenase pathway can have utility is in myocardial infarction. Studies in dogs with the dual inhibitor, BW755-C, demonstrated that the area of infarction following coronary occlusion was reduced, and such reduction was attributed to inhibition of leukocyte infiltration into the ischaemic tissue [See, Mollane et al., *J. Pharmacol. Exp. Therap.*, 228, 510–522 (1984)].

Yet another area of utility for inhibitors of the 5-lipoxygenase pathway is in the area of prevention of rejection of organ transplants. [See, e.g., Foegh et al., *Adv. Prostaglandin, Thromboxane, and Leukotriene Research*, 13, 209–217 (1983)].

Yet another utility for inhibitors of the 5-lipoxygenase pathway is in the treatment of tissue trauma. [See, e.g., Denzliner et al., Science, 230 (4723), 530–332 (1985)].

Furthermore, another area of utility for inhibitors of the 5-lipoxygenase pathway is in the treatment of inflammatory reaction in the central nervous system, including multiple sclerosis. [see, e.g., Mackay et al., *Clin. Exp. Immunol.*, 15, 471–482 (1973).

Another area of utility for inhibitors of the 5-lipoxygenase pathway is in the treatment of asthma. [see, e.g., Ford-Hutchinson, *J. Allergy Clin. Immunol.*, 74, 437-440 (1984).

This invention relates to a pharmaceutical composition comprising an effective, 5-lipoxygenase pathway inhibiting amount of a compound of Formula (IA), or a pharmaceutically acceptable salt thereof, and a pharmaceutically acceptable carrier or diluent. As stated above, all of the compounds of Formula (IA) are within the scope of Formula (I).

The compounds of Formula (I) are administered in conventional dosage forms prepared by combining a compound of Formula (I) or a salt thereof in an amount sufficient to produce activity with a standard pharmaceutical carrier according to conventional procedures. These procedures may involve mixing, granulating and compressing or dissolving the ingredients as appropriate to the desired preparation. The resulting pharmaceutical compositions which comprise an effective, 5-lipoxygenase pathway inhibiting amount of a compound of Formula (IA) are also objects of this invention.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include a time delay material well known to the art, such as glyceryl monostearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 g. If a liquid carrier is used, the preparation will be in the form of a syrup, emulsion, soft gelatin capsule, sterile injectable liquid such as an ampule or a nonaqueous liquid suspension.

To obtain a stable water soluble dose form, a pharmaceutically acceptable acid addition salt, preferably hydrochloride or sulfate, of a compound of Formula (I) is dissolved in an aqueous solution of an organic or inorganic acid, such as a 0.3M solution of succinate acid or, preferably, citric acid. In addition to sulfate and hydrochloride, methanesulfonate, phosphate and hydrobromide are exemplary of other water soluble salts.

Preferably, each parenteral dosage unit will contain the active ingredient in an amount of from about 50 mg to about 500 mg.

The compounds of Formula (I) may be administered topically to a mammal in need of the inhibition of the 5-lipoxygenase pathway of arachidonic acid metabolism. Thus, the compounds of Formula (I) may be administered topically in the treatment or prophylaxis of inflammation in an animal, including man and other mammals and may be used in the relief of rheumatoid spondylitis, osteoarthritis, gouty arthritis and other arthritic conditions, inflamed joints, exzema, psoriasis or other inflammatory skin conditions such as sunburn; inflammatory eye conditions including conjunctivitis; pyresis, pain and other conditions associated with inflammation.

The amount of a compound of Formula (I) (hereinafter referred to as the active ingredient) required for therapeutic effect on topical administration will, of course, vary with the compound chosen, the nature and severity of the inflammatory condition and the animal undergoing treatment, and is ultimately at the discretion of the physician. A suitable anti-inflammatory dose of an active ingredient is 1 ug to 500 mg of base for topical administration, the most preferred dosage being 1 ug to 1000 ug, for example, 5 to 25 ug administered two or three times daily.

By topical administration is meant non-systemic administration and includes the application of a compound of Formula (I) externally to the epidermis, to the buccal cavity and instillation of such a compound into the ear, eye and nose, and where the compound does not significantly enter the blood stream. By systemic administration is meant oral, intravenous, intraperitoneal and intramuscular administration.

While it is possible for an active ingredient to be administered alone as the raw chemical, it is preferable to present it as a pharmaceutical formulation. The active ingredient may comprise, for topical administration, from 0.001% to 10% w/w, e.g. from 1% to 2% by weight of the formulation although it may comprise as much as 10% w/w but preferably not in excess of 5% w/w and more preferably from 0.1% to 1% w/w of the formulation.

The topical formulations of the present invention, both for veterinary and for human medical use, comprise an active ingredient together with one or more acceptable carrier(s) thereof and optionally any other therapeutic ingredient(s). The carrier(s) must be 'acceptable' in the sense of being compatible with the other ingredients of the formulation and not deleterious to the recipient thereof.

Formulations suitable for topical administration include liquid or semi-liquid preparations suitable for penetration through the skin to the site of inflammation such as: liniments, lotions, creams, ointments or pastes, and drops suitable for administration to the eye, ear or nose.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98°-100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as steric or oleic acid together with an alcohol such as prolylene glycol or macrogols. The formulation may incorporate any suitable surface active agent such as an anionic, cationic or non-ionic sulfactant such as sorbitan esters or polyoxyethylene derivatives thereof. Suspending agents such as natural gums, cellulose derivatives or inorganic materials such as silicaceous silicas, and other ingredients such as lanolin, may also be included.

The compounds of Formula (I) may also be administered by inhalation. By "inhalation" is meant intranasal and oral inhalation administration. Appropriate dosage forms for such administration, such as an aerosol formulation or a metered dose inhaler, may be prepared by conventional techniques. The preferred daily dosage amount of a compound of Formula (I) administered by inhalation is from about 10 mg to about 200 mg per day.

This invention relates to a method of treating a disease state mediated by the 5-lipoxygenase pathway in an animal in need thereof, including humans and other mammals, provided that such animal is in need of treatment of a 5-lipoxygenase pathway mediated disease other than, rheumatoid arthritis, which comprises administering to such animal an effective, 5-lipoxygenase pathway inhibiting amount of a Formula (I) compound or a pharmaceutically acceptable salt thereof. By "treating" is meant either prophylactic or therapeutic therapy. By "mediated" is meant caused by or exacerbated by. The formula (I) compound is administered to an animal in need of inhibition of the 5-lipoxygenase pathway in an amount sufficient to inhibit the 5-lipoxygenase pathway. Such Formula (I) compound can be administered to such animal in a conventional dosage form prepared by combining the Formula (I) compound with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. The route of administration may be parenteral, by inhalation or topical. The term parenteral as used herein includes intravenous, intramuscular, subcutaneous, intrarectal, intravaginal or intraperitoneal administration. The subcutaneous and intramuscular forms of parenteral administration are generally preferred. The daily dosage regimen for parenteral administration will preferably be from about 100 mg to about 1.5 g per day. The daily dosage regimen for topical administration will preferably be from about 2 mg to about 10 mg. per site of administration.

It will be recognized by one of skill in the art that the optimal quantity and spacing of individual dosages of the Formula (I) compound will be determined by the nature and extent of the condition being treated, the form, route and site of administration, and the particular animal being treated, and that such optimums can be determined by conventional techniques. It will also be appreciated by one of skill in the art that the optimal course of treatment, i.e., the number of doses of the Formula (I) compound given per day for a defined number of days, can be ascertained by those skilled in the art using conventional course of treatment determination tests.

EXAMPLES

Without further elaboration, it is believed that one skilled in the art can, using the preceding description, utilize the present invention to its fullest extent. The following examples are, therefore, to be construed as merely illustrative and not a limitation of the scope of the present invention in any way.

SYNTHESIS EXAMPLES

Example 1

2-2'-[1,3-propan-2-onediylbis(thio)]bis[5-(4-pyridyl)-4-(4-fluorophenyl)-1H-imidazole]

A suspension of 4-(4-pyridyl)-5-(4-fluorophenyl)-[1H]-imidazole-2-thione (5.0 g, 0.0184 mol), prepared by the method of Lantos et al., *J. Med. Chem.*, 27, 72–75 (1984), and 1,3-dichloropropanone (1.15 g, 0.00906 mol) in ethanol (30 ml) was refluxed for 90 minutes, and then the mixture was cooled. The resulting precipitate was filtered, washed with ether and recrystallized from ethanol to give the title compound as the dihydrochloride salt (hydrate), melting point (mp) 251°–252° C. (dec).

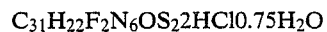

Calculated: 54.51%C; 3.76%H; 12.30%N. Found: 54.46%C; 3.82%H; 12.46%N.

UTILITY EXAMPLES

In the following Examples male Balb/c mice (20–28 g) were used. All mice were obtained from Charles River Breeding Laboratories, Kingston, N.Y. Within a single experiment, mice were sex and age matched.

In the following examples, reagents used were employed as follows:

Compounds of Formula (I), indomethacin, naproxen, and ibuprofen were each used as the free base. The compounds were homogenized in 0.5% tragacanth. Compounds were administered by gavage at the indicated dose in a final volume of 10 ml/kg.

For in vitro experiments, compounds were dissolved at appropriate concentrations in ethanol (final concentration 1.0%) and then diluted to final concentrations using the buffers indicated in the text.

I. METHODS

Arachidonic Acid-Induced Mouse Ear Inflammation

Arachidonic acid in acetone (2 mg/20 μl) was applied to the inner surface of the left ear. The thickness of both ears was then measured with a dial micrometer one hour after treatment, and the data were expressed as the change in thickness ($10^{-3}$ cm) between treated and untreated ears.

Test compounds were given orally in 0.5% tragacanth at the times indicated in the test prior to the topical application of arachidonic acid.

Parenteral administration of compound was accomplished by subcutaneous injection of solution as indicated.

Assay of 5-Lipoxygenase Activity

The activities of these enzymes in extracts of RBL-1 cells were assayed using the method of Jakschik and Lee, Nature, 287, 51–52 (1980). RBL-1 cells were obtained from the American Type Culture Collection (#CRL 1378) and were grown at 37° C. (5% $CO_2$ in air) in spinner culture in MEM supplemented with 10% heat inactivated fetal calf serum. Harvested cells were washed with 50 mM sodium phosphate buffer, pH 7.0, containing 1 mM EDTA and 0.1% gelatin, resuspended in fresh buffer ($5 \times 10^7$ cells/ml) and disrupted by nitrogen cavitation using the Parr bomb at 750 psi for 10 min. The broken cell extract was then centrifuged at $10,000 \times g$ for 20 minutes (min) and the supernatant centrifuge at $100,000 \times g$ for 60 min. Aliquots (0.25 mls) of the supernatant were preincubated with or without drugs for 10 min, after which 12 mM $CaCl_2$ was added and the reaction was initiated with 2.5 ml of 2.5 $\mu M$ arachidonic acid-1-$^{14}C$ (final concentration was 25 $\mu M$; specific activity 20,000 dpm/nmole). After incubation for 5 min at 37° C., the reaction was terminated by addition of 2 volumes (0.5 ml) ice cold acetone and the sample was allowed to deproteinize on ice for 10 min prior to centrifugation at $1,000 \times g$ for 10 min. The deproteinized supernatant was adjusted to pH 3.5 with 2N formic acid and extracted with 2 volumes of ice cold ethyl acetate. The extracted samples were dried under argon, redissolved in ethyl acetate and applied to Whatman LK5D thin layer chromatography (TLC) plates which were developed using the A-9 solvent system [organic phase of ethyl acetate: 2,2,5-trimethylpentane:acetic acid:water (110:50:20:10)] described by Hamberg and Samuelsson, J. Biol. Chem., 241, 257–263 (1966). Arachidonic acid, 5-HETE, $LTB_4$ and $PGD_2$ were quantified with a Berthold LB 2832 autoscanner.

Under these conditions, only the 5-lipoxygenase pathway metabolites were detectable. The 5-HETE and di-HETEs were formed at a linear rate, and substantial amounts of the arachidonic acid-1-$^{14}C$ substrate were utilized.

Drug-induced effects on enzyme activities are described as the concentration of drug causing a 50% inhibition of metabolite synthesis ($IC_{50}$).

II. RESULTS

The Effect of Compounds of Formula (I) on Arachidonic Acid-induced Inflammation Compounds of Formula (I) dosed orally produce insignificant inhibition of the edematous response normally seen 1 hour after the application of 2 mg of arachidonic acid to the ear. The cyclooxygenase inhibitors, indomethacin (10 mg/kg, p.o.), ibuprofen (250 mg/kg, p.o.) and naproxen (100 mg/kg, p.o.) also did not exhibit detectable antiinflammatory activity in this assay, despite use at near maximally tolerated doses.

The Effect of Compounds of Formula (I) on Arachidonic Acid Metabolism

Experiments using a soluble extract preparation of RBL-1 cells containing only lipoxygenase activity confirmed the inhibitory effects of compounds of Formula (I) on $LTB_4$ production (Table II) and 5-HETE product (Table III). The data in Table II shows that compounds of Formula (I) are significant inhibitors of the 5-lipoxygenase pathway as confirmed by their inhibition of $LTB_4$, a 5-lipoxygenase pathway product. The data in Table III also shows that compounds of Formula (I) are significant inhibitors of the 5-lipoxygenase pathway as confirmed by their inhibition of 5-HETE, a 5-lipoxygenase pathway product. Thus, although the compounds of Formula (I) are insignificant inhibitors of arachidonic acid-induced inflammation when dosed orally (Table 1), the data of Table II and Table III confirm that such compounds are indeed inhibitors of the 5-lipoxygenase pathway.

TABLE I

The Effect of Compounds of Formula (I) on Arachidonic Acid Induced Ear Swelling

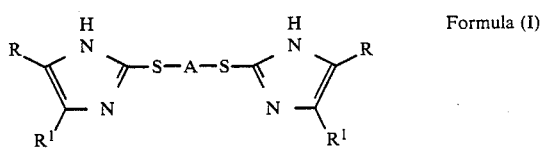

Formula (I)

| Compound Number | R | $R^1$ | A | % Inhibition[a,b] of Ear Swelling |
|---|---|---|---|---|
| 1 | 4-fluorophenyl | 4-fluorophenyl | $CH_2CH_2$ | N (p.o.) |
| 2 | 4-pyridyl | 4-fluorophenyl | $CH_2C(O)CH_2$ | NS (p.o.) |
| 3 | 4-fluorophenyl | 4-fluorophenyl | $CH_2C(O)CH_2$ | NT |

[a] screened at 50 mg/kg s.c. or i.p. unless indicated as oral dosing (p.o.).
[b] * = $p < .05$,  = $p < .01$, * = $p < .001$, NS = not significant, NT = not tested.

TABLE II

The Effect of Compounds of Formula (I) on 5-Lipoxygenase Activity

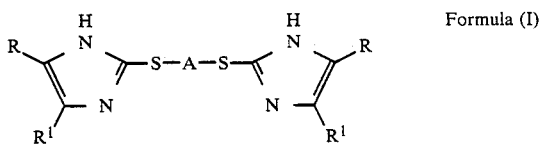

Formula (I)

| Compound Number | R | $R^1$ | A | $LTB_4$ $IC_{50}$ ($\mu M$) |
|---|---|---|---|---|
| 1 | 4-fluorophenyl | 4-fluorophenyl | $CH_2CH_2$ | 3.3 |
| 2 | 4-pyridyl | 4-fluorophenyl | $CH_2C(O)CH_2$ | 0.65 |
| 3 | 4-fluorophenyl | 4-fluorophenyl | $CH_2C(O)CH_2$ | 1.6 |

[a] $IC_{50}$ determined on $LTB_4$ production by RBL-1 high speed supernatant.

TABLE III

The Effect of Compounds of Formula (I) on
5-Lipoxygenase Activity (5-HETE Production)

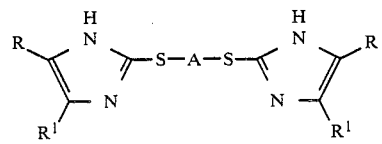

Formula (I)

| Compound Number | R | $R^1$ | A | 5-HETE[a] $IC_{50}$ ($\mu M$) |
|---|---|---|---|---|
| 1 | 4-fluorophenyl | 4-fluorophenyl | $CH_2CH_2$ | 18.5 |
| 2 | 4-pyridyl | 4-fluorophenyl | $CH_2C(O)CH_2$ | 1.7 |
| 3 | 4-fluorophenyl | 4-fluorophenyl | $CH_2C(O)CH_2$ | 5.3 |

[a]$IC_{50}$ determined on 5-HETE production by RBL-1 high speed supernatant.

EXAMPLE A

Injectable Parenteral Composition

A pharmaceutical composition of this invention in a form suitable for administration by injection is prepared by stirring 10% by weight of a compound of Formula (IA) in 10% by volume propylene glycol and water.

EXAMPLE B

Ointment Composition

Compound of Formula (IA) 1.0 g
White soft paraffin to 100.0 g

The compound of Formula (IA) is dispersed in a small volume of the vehicle and this dispersion is gradually incorporated into the bulk to produce a smooth, homogeneous product which is filled into collapsible metal tubes.

EXAMPLE C

Topical Cream Composition

Compound of Formula (IA) 1.0 g
Polawax GP 200 20.0 g
Lanolin Anhydrous 2.0 g
White Beeswax 2.5 g
Methyl hydroxybenzoate 0.1 g
Distilled Water to 100.0 g The polawax, beeswax and lanolin are heated together at 60° C. and a solution of methyl hydroxybenzoate is added. Homogenization is achieved using high speed stirring and the temperature is allowed to fall to 50° C. The compound of Formula (IA) is added and dispersed throughout, and the composition is allowed to cool with slow speed stirring.

EXAMPLE D

Topical Lotion Composition

Compound of Formula (IA) 1.0 g
Sorbitan Monolaurate 0.6 g
Polysorbate 20 0.6 g
Cetostearyl Alcohol 1.5 g
Glycerin 6.0 g
Methyl hydroxybenzoate 0.2 g
Purified Water B.P. to 100.00 ml The methyl hydroxybenzoate and glycerin are dissolved in 70 ml of the water at 75°. The sorbitan monolaurate, polysorbate 20 and cetostearyl alcohol are melted together at 75° C. and added to the aqueous solution. The resulting emulsion is homogenized, allowed to cool with continuous stirring and the compound of Formula (IA) is added as a suspension in the remaining water. The whole suspension is stirred until homogenized.

EXAMPLE E

Eye Drop Composition

Compound of Formula (IA) 0.5 g
Methyl Hydroxybenzoate 0.01 g
Propyl Hydroxybenzoate 0.04 g
Purified Water B.P. to 100.00 ml The methyl and propyl hydroxybenzoates are dissolved in 70 ml purified water at 75° C. and the resulting solution is allowed to cool. The compound of Formula (IA) is then added, and the solution is made up to 100 ml with purified water. The solution is sterilized by filtration through a membrane filter (0.22 mu m pore size) and packed aseptically into suitable sterile containers.

EXAMPLE F

Composition for Administration by Inhalation

For an aerosol container with a capacity of 15–20 ml: mix 10 mg of a compound of Formula (IA) with 0.1–0.2% of a lubricating agent, such as Span 85 or oleic acid, and disperse such mixture in a propellane (c.a.), such as freon, preferably a combination of freon 114 and freon 12, and put into an appropriate aerosol container adapted for either intranasal or oral inhalation administration.

EXAMPLE G

Composition for Administration by Inhalation

For an aerosol container with a capacity of 15–20 ml: Dissolve 10 mg of a compound of Formula (IA) in ethanol (6–8 ml) and disperse such in a propellant (c.a.), such as freon, preferably a combination of freon 114 and freon 12, and put into an appropriate aerosol container adapted for either intranasal or oral inhalation administration.

What is claimed is:

1. A method of treating a disease mediated by the 5-lipoxygenase pathway in an animal in need thereof, provided such animal is in need of treatment of one of the 5-lipoxygenase pathway mediated diseases of inflammatory bowel disease, psoriasis, gout, myocardial infarction, organ transplant rejection, tissue trauma, multiple sclerosis, asthma, rheumatoid spondylitis, osteoarthritis, gouty arthritis, inflamed joints, exzema, conjunctivitis or pyresis, which comprises administering parenterally, topically or by inhalation to such animal an effective, non-toxic 5-lipoxygenase pathway inhibiting amount of a compound of the formula

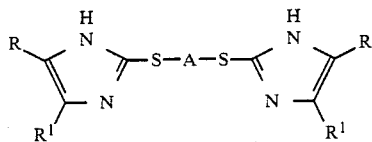

wherein:

A is $CH_2CH_2$ or $CH_2C(O)CH_2$; and

R and $R^1$ are pyridyl or one of R and $R^1$ is pyridyl and the other is monosubstituted phenyl wherein said substituent is selected from halo;

or a pharmaceutically acceptable salt thereof.

2. The method of claim 1 wherein A is $CH_2C(O)CH_2$, R is 4-pyridyl and $R^1$ is 4-fluorophenyl.

3. The method of claim 1 wherein the administration is parenteral and the amount of compound administered is selected from about 50 mg to about 500 mg.

4. The method of claim 1 wherein the amount of compound administered per day is from about 50 mg to about 1000 g.

5. The method of claim 1 wherein the compound is administered by inhalation.

6. The method of claim 5 wherein the amount of compound administered is from about 10 mg to about 200 mg per day.

7. The method of claim 1 wherein the compound is administered topically.

8. The method of claim 7 wherein the amount of compound administered per dose is 1 μg to 1000 μg.

* * * * *